(12) United States Patent
Steinke

(10) Patent No.: US 11,577,069 B2
(45) Date of Patent: Feb. 14, 2023

(54) METHOD AND APPARATUS FOR TAGGING STIMULATION FIELD MODELS WITH ASSOCIATED STIMULATION EFFECT TYPES

(71) Applicant: Boston Scientific Neuromodulation Corporation, Valencia, CA (US)

(72) Inventor: G. Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 311 days.

(21) Appl. No.: 16/902,064

(22) Filed: Jun. 15, 2020

(65) Prior Publication Data

US 2020/0406021 A1    Dec. 31, 2020

Related U.S. Application Data

(60) Provisional application No. 62/867,478, filed on Jun. 27, 2019.

(51) Int. Cl.

| | |
|---|---|
| *A61N 1/02* | (2006.01) |
| *A61N 1/36* | (2006.01) |
| *A61N 1/372* | (2006.01) |
| *A61N 1/05* | (2006.01) |
| *G16H 20/30* | (2018.01) |
| *G16H 40/63* | (2018.01) |

(52) U.S. Cl.
CPC ......... *A61N 1/025* (2013.01); *A61N 1/36128* (2013.01); *G16H 20/30* (2018.01); *G16H 40/63* (2018.01); *A61N 1/0534* (2013.01); *A61N 1/0551* (2013.01); *A61N 1/37247* (2013.01)

(58) Field of Classification Search
CPC .. A61N 1/025; A61N 1/36128; A61N 1/0534; A61N 1/0551; A61N 1/37247; A61N 1/3615; A61N 1/36167; A61N 1/36182; A61N 1/36146; A61N 1/0526
See application file for complete search history.

(56) References Cited

U.S. PATENT DOCUMENTS

| | | |
|---|---|---|
| 7,647,116 B2 | 1/2010 | Bauhahn |
| 8,190,250 B2 | 5/2012 | Moffitt |

(Continued)

*Primary Examiner* — Mallika D Fairchild
(74) *Attorney, Agent, or Firm* — Schwegman Lundberg & Woessner, P.A.

(57) ABSTRACT

An example of a system for programming neurostimulation according to a stimulation configuration may include stimulation configuration circuitry, volume definition circuitry, stimulation effect circuitry, and recording circuitry. The stimulation configuration circuitry may be configured to determine the stimulation configuration. The volume definition circuitry may be configured to determine stimulation field model(s) (SFM(s)) each representing a volume of tissue activated by the neurostimulation. The stimulation effect circuitry may be configured to determine a stimulation effect type for each tagging point specified for the SFM(s) and to tag the SFM(s) at each tagging point with the stimulation effect type determined for that tagging point. The stimulation effect type for each tagging point is a type of stimulation resulting from the neurostimulation as measured at that tagging point. The recording circuitry may be configured to generate SFM data representing the determined SFM(s) with the stimulation effect type tagged at each tagging point.

20 Claims, 9 Drawing Sheets

(56) References Cited

U.S. PATENT DOCUMENTS

| | | |
|---|---|---|
| 8,233,984 B2 | 7/2012 | Forsberg et al. |
| 8,380,321 B2 | 2/2013 | Goetz et al. |
| 8,706,250 B2 | 4/2014 | Zhu et al. |
| 8,849,411 B2 | 9/2014 | Moffitt et al. |
| 8,918,183 B2 | 12/2014 | Carlton et al. |
| 8,934,979 B2 | 1/2015 | Moffitt |
| 8,996,123 B2 | 3/2015 | Goetz et al. |
| 9,792,412 B2 | 10/2017 | Moffitt et al. |
| 2011/0106213 A1 | 5/2011 | Davis et al. |
| 2012/0165898 A1* | 6/2012 | Moffitt ............... A61N 1/36128 607/45 |

\* cited by examiner

METHOD AND APPARATUS FOR TAGGING STIMULATION FIELD MODELS WITH ASSOCIATED STIMULATION EFFECT TYPES

CLAIM OF PRIORITY

This application claims the benefit of priority under 35 U.S.C. § 119(e) of U.S. Provisional Patent Application Ser. No. 62/867,478, filed on Jun. 27, 2019, which is herein incorporated by reference in its entirety.

TECHNICAL FIELD

This document relates generally to medical devices and more particularly to a method and system for encoding stimulation effect types in data structure and presentation of stimulation field models (SFMs).

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. The human nervous systems use neural signals having sophisticated patterns to communicate various types of information, including sensations of pain, pressure, temperature, etc. It may interpret an artificial stimulation with a simple pattern of stimuli as an unnatural phenomenon, and respond with an unintended and undesirable sensation and/or movement. Also, as the condition of the patient may change while receiving a neurostimulation therapy, the pattern of neurostimulation pulses applied to the patient may need to be changed to maintain efficacy of the therapy while minimizing the unintended and undesirable sensation and/or movement. While modern electronics can accommodate the need for generating sophisticated pulse patterns that emulate natural patterns of neural signals observed in the human body, the capability of a neurostimulation system depends on how the stimulation parameters can be determined for a patient. Such determination can be facilitated by analyzing effects of the stimulation parameters in activating target tissue in the patient.

SUMMARY

An example (e.g., "Example 1") of a system for programming a stimulation device to deliver neurostimulation to tissue of a patient according to a stimulation configuration may include stimulation configuration circuitry, volume definition circuitry, stimulation effect circuitry, and recording circuitry. The stimulation configuration circuitry may be configured to determine the stimulation configuration. The volume definition circuitry may be configured to determine one or more stimulation field models (SFMs) each representing a volume of the tissue activated by the delivery of the neurostimulation according to the stimulation configuration. The stimulation effect circuitry may be configured to determine a stimulation effect type for each tagging point specified for the one or more SFMs and to tag the one or more SFMs at each tagging point with the stimulation effect type determined for that tagging point. The stimulation effect type for each tagging point is a type of stimulation resulting from the delivery of the neurostimulation according to the stimulation configuration as measured at that tagging point. The recording circuitry may be configured to generate SFM data representing the determined one or more SFMs with the stimulation effect type tagged at each tagging point.

In Example 2, the subject matter of Example 1 may optionally be configured to further include a presentation device and presentation circuitry. The presentation circuitry is configured to present the determined one or more SFMs with visual indication of the stimulation effect type for each tagging point on the presentation device using the generated SFM data.

In Example 3, the subject matter of Example 2 may optionally be configured such that the presentation device includes a display screen, and the presentation circuitry is configured to display on the display screen visually distinctive features assigned to various stimulation effect types.

In Example 4, the subject matter of Example 3 may optionally be configured such that the visually distinctive features include various degrees of shading.

In Example 5, the subject matter of Example 3 may optionally be configured such that the visually distinctive features include various degrees of opacity.

In Example 6, the subject matter of Example 3 may optionally be configured such that the visually distinctive features include various textures.

In Example 7, the subject matter of Example 3 may optionally be configured such that the visually distinctive features include various colors.

In Example 8, the subject matter of any one or any combination of Examples 1 to 7 may optionally be configured such that the stimulation effect circuitry is configured to determine a polarity of the stimulation effect type.

In Example 9, the subject matter of Example 8 may optionally be configured such that the stimulation effect circuitry is further configured to determine a neurostimulation pulse type of the stimulation effect type.

In Example 10, the subject matter of any one or any combination of Examples 1 to 9 may optionally be configured such that the stimulation effect circuitry is configured to determine a voltage profile for each tagging point being a voltage signal measured at the tagging point and representing the stimulation field at the tagging point.

In Example 11, the subject matter of Example 10 may optionally be configured such that the stimulation effect circuitry is further configured to extract one or more features as a representation of the stimulation effect type from at least one of the voltage profile or one or more derivatives of the voltage profile.

In Example 12, the subject matter of any one or any combination of Examples 1 to 11 may optionally be configured such that the stimulation effect circuitry is configured to determine the stimulation effect type for each SFM of the one or more SFMs.

In Example 13, the subject matter of any one or any combination of Examples 1 to 11 may optionally be configured such that the stimulation effect circuitry is configured to determine the stimulation effect type for each grid point in or on the one or more SFMs.

In Example 14, the subject matter of any one or any combination of Examples 1 to 11 may optionally be configured such that the stimulation effect circuitry is configured to determine the stimulation effect type for each voxel within the one or more SFMs.

In Example 15, the subject matter of any one or any combination of Examples 1 to 14 may optionally be configured to further include a programming control circuit and a user interface. The programming control circuit is configured to generate a plurality of stimulation parameters controlling delivery of the neurostimulation according to a stimulation configuration, the neurostimulation delivered through one or more electrodes of the plurality of electrodes. The user interface includes a stimulation control circuit that includes at least the stimulation configuration circuitry, the volume definition circuitry, the stimulation effect circuitry, and the recording circuitry.

An example (e.g., "Example 16") of a method for programming a stimulation device to deliver neurostimulation to tissue of a patient according to a stimulation configuration is also provided. The method may include determining the stimulation configuration using a processor; determining one or more stimulation field models (SFMs) using the processor, determining a stimulation effect type for each tagging point using the processor, tagging the one or more SFMs at each tagging point specified for the one or more SFMs with the stimulation effect type determined for that tagging point using the processor, and generating SFM data using the processor. The one or more SFMs each represent a volume of the tissue activated by the delivery of the neurostimulation according to the stimulation configuration. The stimulation effect type for each tagging point is a type of stimulation resulting from the delivery of the neurostimulation according to the stimulation configuration as measured at that tagging point. The SFM data represent the determined one or more SFMs with the stimulation effect type tagged at each tagging point.

In Example 17, the subject matter of Example 16 may optionally further include displaying the determined one or more SFMs with visual indication of the stimulation effect type for each tagging point on a display screen and displaying visually distinctive features assigned to various stimulation effect types on the display screen.

In Example 18, the subject matter of displaying the visually distinctive features as found in Example 17 may optionally include displaying at least one of various degrees of shading, various degrees of opacity, various textures, or various colors.

In Example 19, the subject matter of determining the stimulation effect type as found in any one or any combination of Examples 16 to 18 may optionally include determining a polarity.

In Example 20, the subject matter of determining the stimulation effect type as found in any one or any combination of Examples 16 to 19 may optionally include determining a neurostimulation pulse type.

In Example 21, the subject matter of determining the stimulation effect type as found in any one or any combination of Examples 16 to 20 may optionally include determining a voltage profile for each tagging point being a voltage signal measured at the tagging point and representing the stimulation field at the tagging point.

In Example 22, the subject matter of determining the stimulation effect type as found in Example 21 may optionally further include extracting one or more features as a representation of the stimulation effect type from at least one of the voltage profile or one or more derivatives of the voltage profile.

In Example 23, the subject matter of determining the stimulation effect type as found in any one or any combination of Examples 16 to 22 may optionally include determining the stimulation effect type for each SFM of the one or more SFMs.

In Example 24, the subject matter of determining the stimulation effect type as found in any one or any combination of Examples 16 to 22 may optionally include determining the stimulation effect type for each grid point in or on the one or more SFMs or voxel within the one or more SFMs.

An example (e.g., "Example 25") of a non-transitory computer-readable storage medium including instructions, which when executed by a system, cause the system to perform a method for programming a stimulation device to deliver neurostimulation to tissue of a patient according to a stimulation configuration is also provided. The method may include determining the stimulation configuration, determining one or more stimulation field models (SFMs) each representing a volume of the tissue activated by the delivery of the neurostimulation according to the stimulation configuration, determining a stimulation effect type for each tagging point specified for the one or more SFMs, tagging the one or more SFMs at each tagging point with the stimulation effect type determined for that tagging point, and generating SFM data representing the determined one or more SFMs with the stimulation effect type tagged at each tagging point. The stimulation effect type for each tagging point is a type of stimulation resulting from the delivery of the neurostimulation according to the stimulation configuration as measured at that tagging point.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
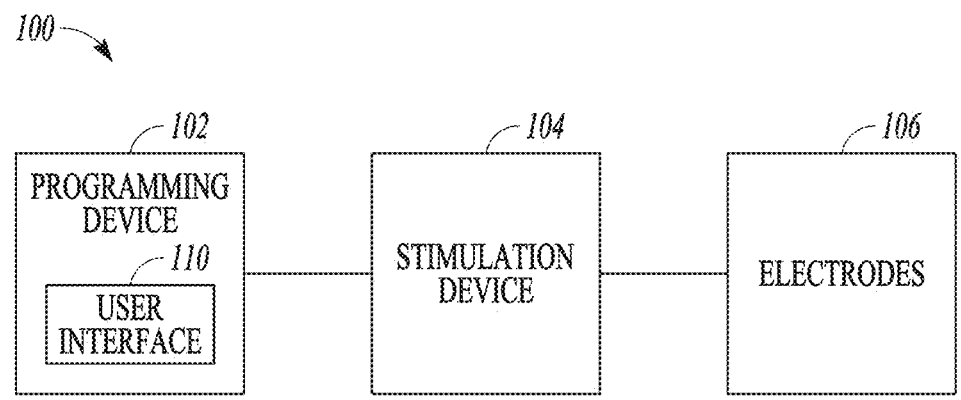
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for providing information for analyzing effects of neurostimulation (also referred to as neuromodulation) including volumes of tissue activated and their underlying electric fields resulting from the neurostimulation. In various embodiments, the neurostimulation can be delivered using a neurostimulation system including an implantable device configured to deliver therapies such as deep brain stimulation (DBS), spinal cord stimulation (SCS), peripheral nerve stimulation (PNS), and vagus nerve stimulation (VNS) and one or more external devices configured to program the implantable device for its operations. The present subject matter can be implemented in such one or more external devices. While DBS is discussed as a specific example, the present subject matter can be applied to analysis of effects of stimulation for various types of neuromodulation therapies.

Based on stimulation parameters controlling the operation of a neurostimulation system, one or more stimulation field models (SFMs), also referred to as volumes of tissue activated (VTAs) or volumes of activation (VOAs), can be estimated and graphically presented. A graphically presented SFM allows for visual observation of how various stimulator and/or lead settings affect volumes of tissue activated in a patient. An example of creating an SFM based on stimulation parameters is discussed in U.S. Pat. No. 8,849,411, "USER-DEFINED GRAPHICAL SHAPES USED AS A VISUALIZATION AID FOR STIMULATOR PROGRAMMING", assigned to Boston Scientific Neuromodulation Corporation, which is herein incorporated by reference in its entirety. In this document, the volume of tissue activated include the volume of tissue where neural activities and/or tissue properties are modulated by delivery of neurostimulation, including but not limited to eliciting and/or blocking of action potentials.

SFMs can be created and displayed to demonstrate effects of various stimulation effect types (resulting from applying the stimulation parameters) in a neurostimulation therapy. In this document, a "stimulation effect type" includes a type of stimulation underlying each SFM as effected from delivery of neurostimulation controlled by the stimulation parameters. The type of stimulation can include the type of the stimulation field effected from the delivery of neurostimulation and/or other one or more definable types of effect of the delivery of neurostimulation. For example, SFMs were created to demonstrate effects of cathodic stimulation in DBS. Later, new data suggested anodic stimulation could provide different effects, including possibly superior effects. This has created a need to study of effects of polarity of stimulation that covers a spectrum of polarities that can be provided by the stimulation parameters. While information such as active anodes and cathodes used in the electrode settings can be encoded (e.g., using "+" and "−" signs and/or colors) into a presentation that also shows the SFMs, currently the presented SFMs include only an overall effect that does not show attribution to stimulation effect types. When multiple stimulation effect types (e.g., anodic and cathodic stimulations) are applied, the resultant SFMs as currently presented do not show their underlying stimulation effect types. Such information is not encoded into the SFMs and hence, is lost when viewed outside of a programming context, for example when the information is desirable for discerning strength of the effects relative to the stimulation effect types. For example, it is possible to create two SFMs that are visually indistinguishable when displayed, with one created using cathodes only and the other created using anodes only. When using each of these two SFMs in subsequent analysis, it is advantageous to know which type of stimulation each volume is associated with. In this simple example, it is possible to associate other meta-data (e.g., polarity of the current on the lead) in order to determine where each type of stimulation is occurring. However, as further discussed later in this document, such a method does not allow for tagging of SFMs with sufficient resolution (e.g., multiple tagging points for each SFM) and complex stimulation effect types (e.g., a stimulation field with a spectrum of polarities).

The present subject matter can encode the underlying stimulation effect types in SFM data structure and display information to allow analysis and visual observation of the contribution of each stimulation effect type to the overall effect. One example of the stimulation effect types includes stimulation polarity. The stimulation polarity can be, for example, color-coded along a polarity spectrum (from anodic to cathodic). Information required for machine-learning prediction can be used to classify and smoothly color the displayed SFM surface and encoded as meta-data in specified SFM points or portions such as voxels. While the stimulation polarity is specifically discussed in this document as an example for illustrative purposes, the present subject matter can be applied for encoding any stimulation effect types into SFM data. Other examples of the stimulation effect types that can be encoded according to the present subject matter include stimulation pulse types (e.g., with or without a pre-pulsing phase, with or without a post-pulsing phase, and/or with passive or active recharge phases) and the goals of these stimulation pulse types (e.g., having effects similar to anodes or cathodes, and/or having effects to lower or raise thresholds of certain target or non-target neural elements)). In various embodiments, the present subject matter can be applied to encode any information related to an SFM in the data representing the SFM, to allow for observation and/or analysis of various factors affecting the SFM.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
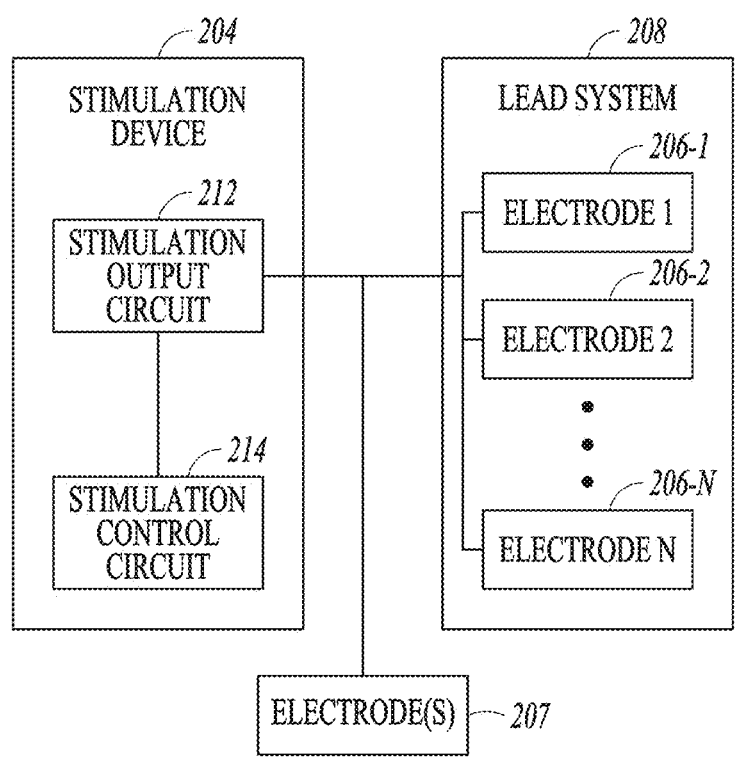
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where $N \geq 2$. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
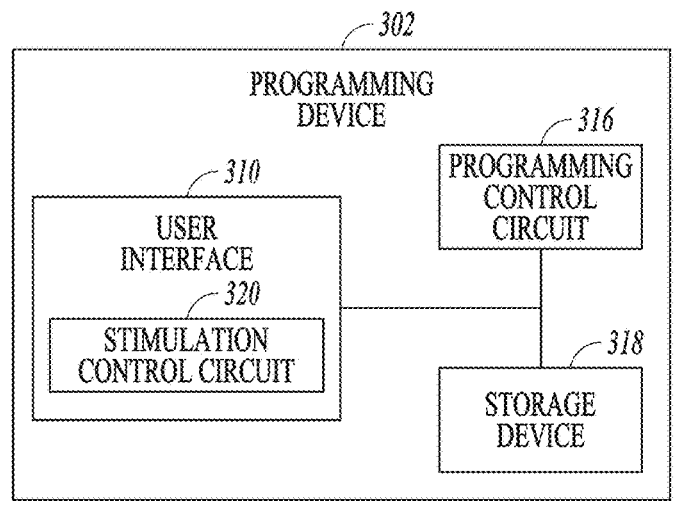
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Programming control circuit 316 generates the plurality of stimulation parameters that controls the delivery of the neurostimulation pulses according to a specified stimulation configuration that can define, for example, stimulation waveform and electrode configuration. User interface 310 represents an embodiment of user interface 110 and includes a stimulation control circuit 320. Storage device 318 stores information used by programming control circuit 316 and stimulation control circuit 320, such as information about a stimulation device that relates the stimulation configuration to the plurality of stimulation parameters and information relating the stimulation configuration to a volume of activation in the patient. In various embodiments, stimulation control circuit 320 can be configured to support one or more functions allowing for programming of stimulation devices, such as stimulation device 104 including its various embodiments as discussed in this document, using SFMS and their underlying stimulation effect types, as discussed below with reference to FIGS. 9-13.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation configuration" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
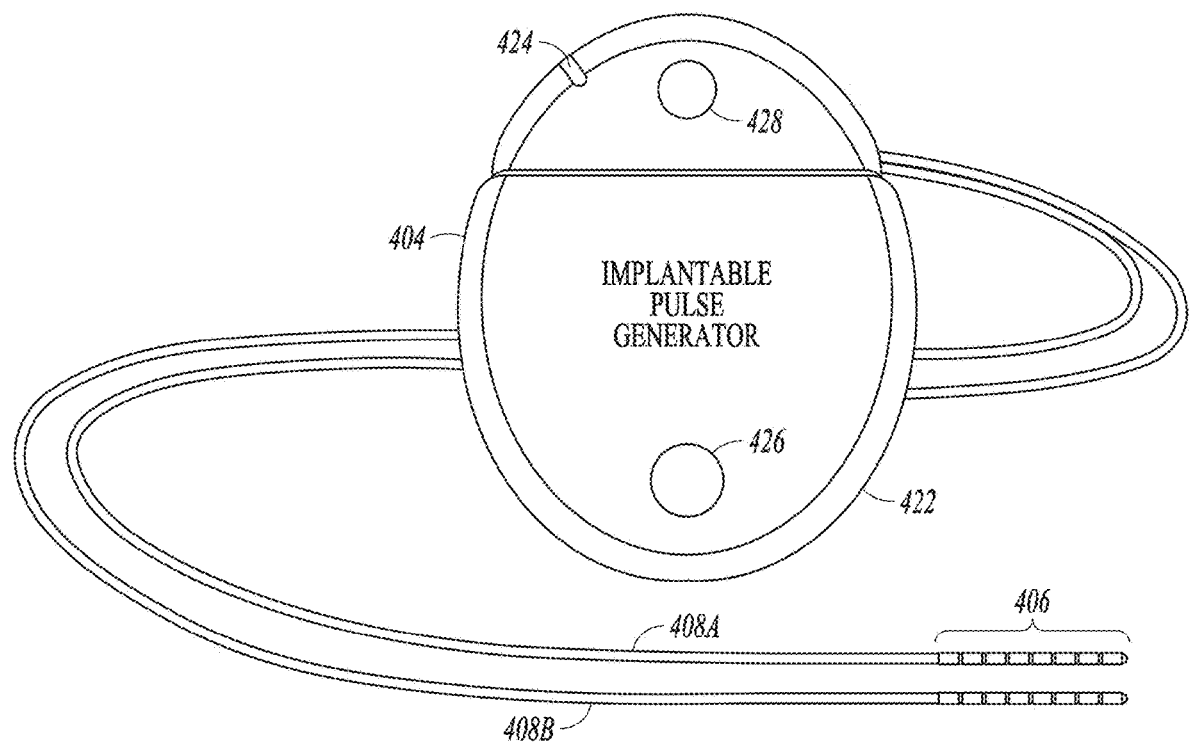
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
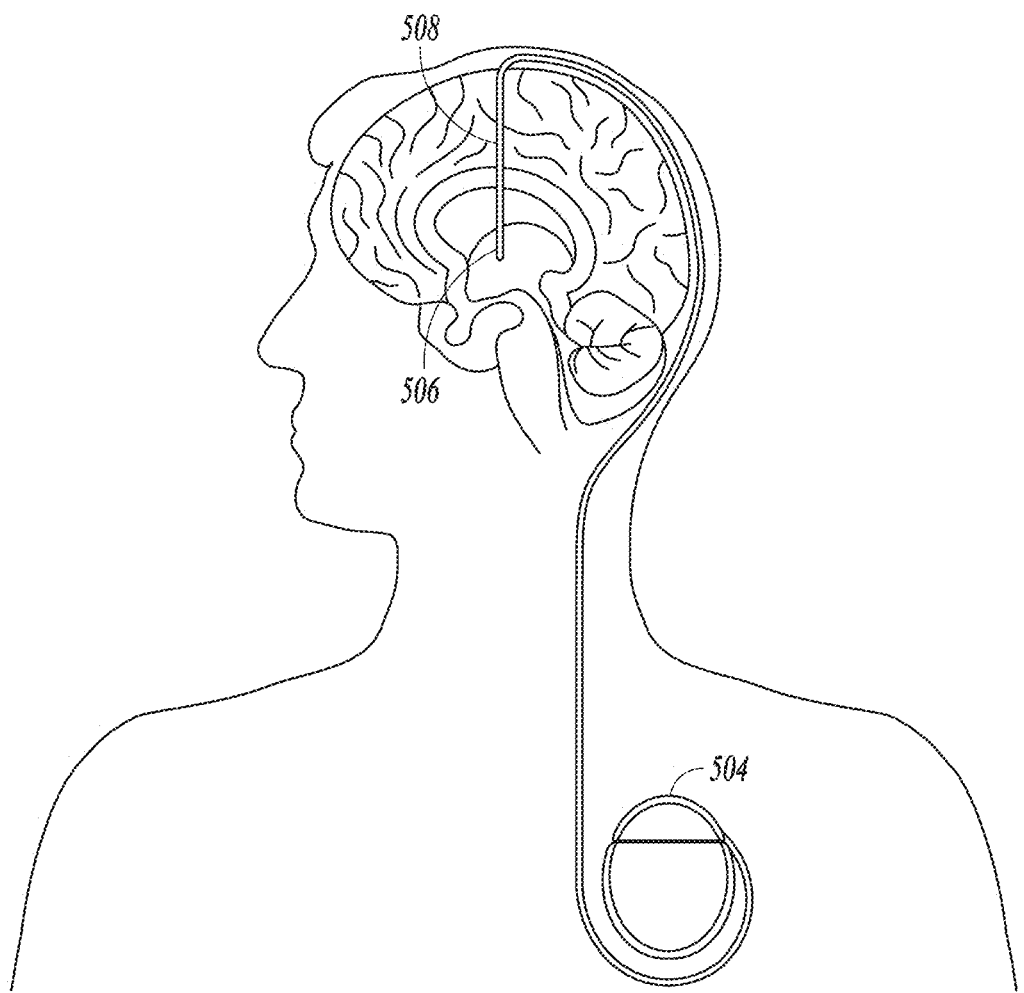
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, and any white matter tracts connecting these and other structures.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode.

Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
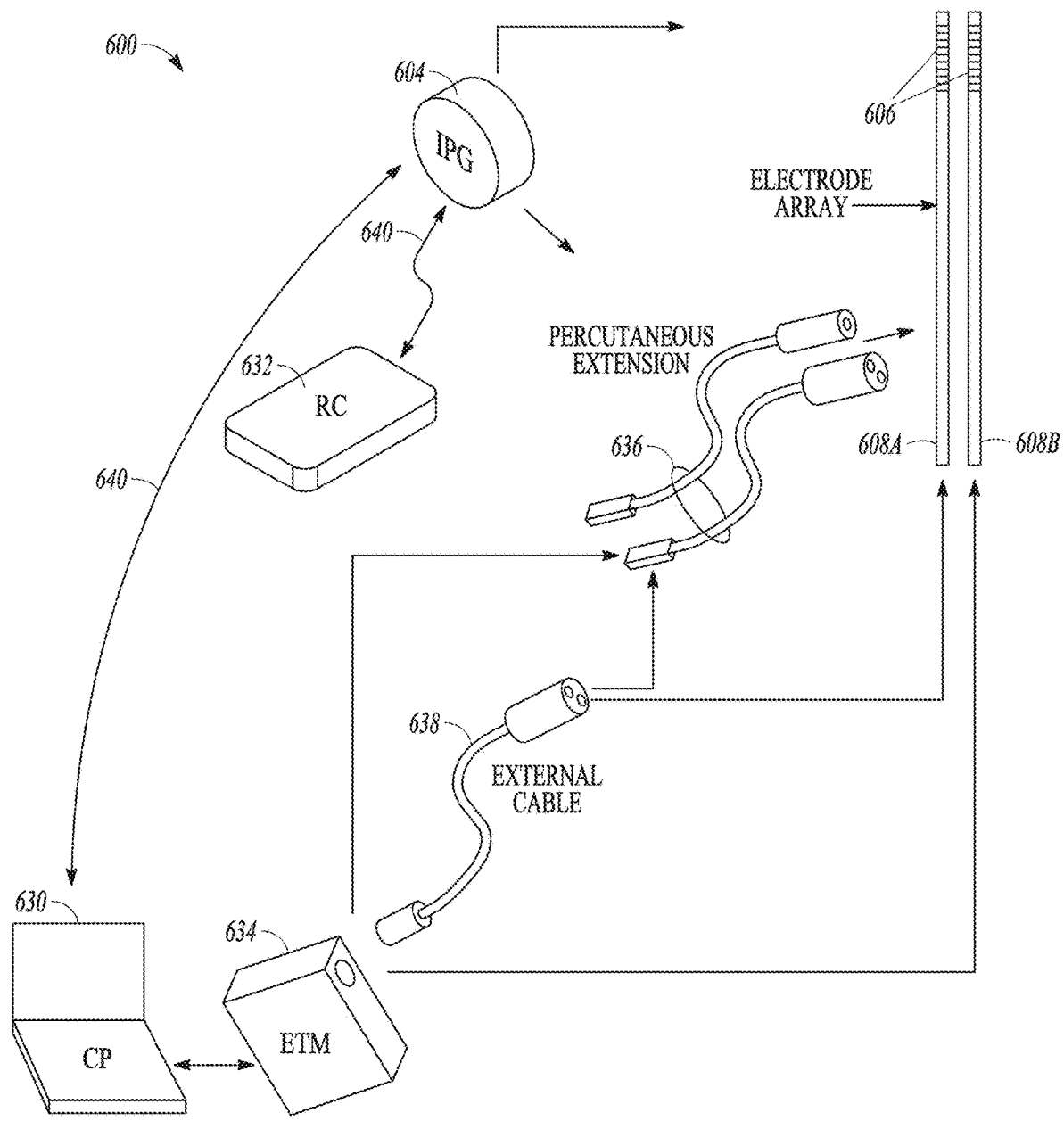
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically, coupled to leads 608A and 608B directly or through percutaneous extension leads 636. ETM 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=λ/2π, where λ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
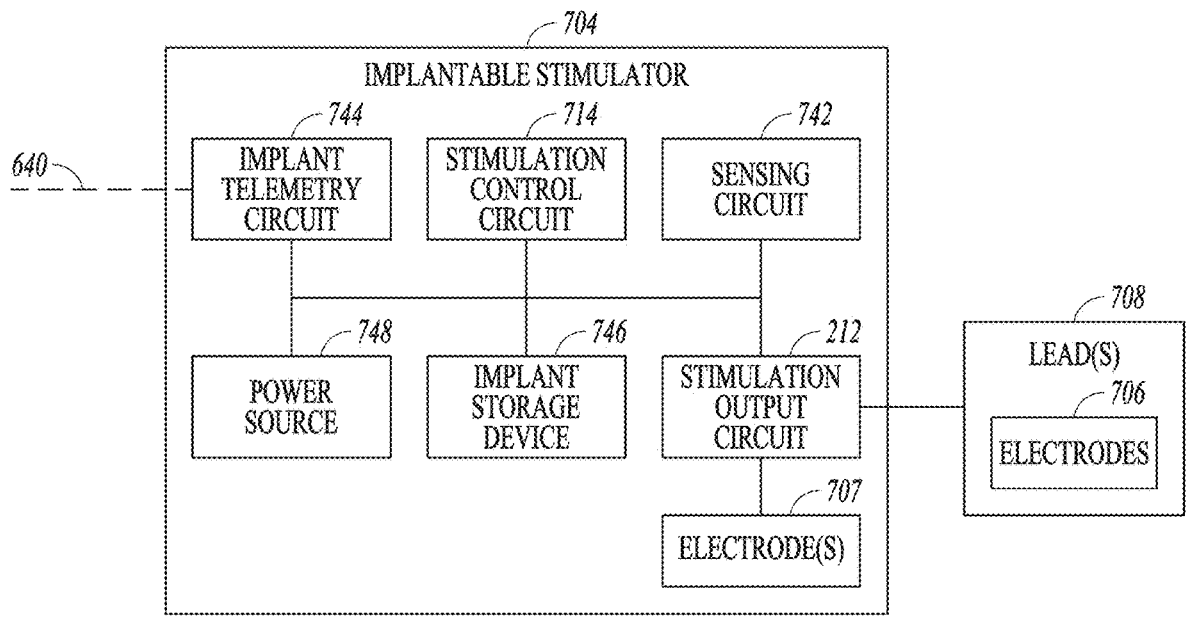
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
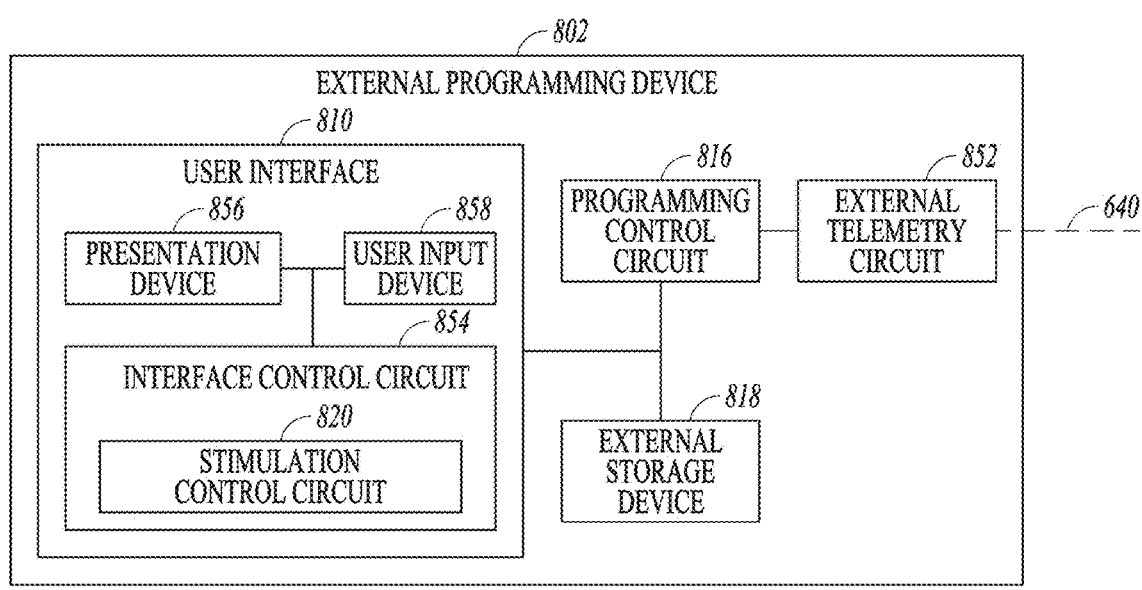
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on a specified stimulation configuration (e.g., the pattern of neurostimulation pulses as represented by one or more stimulation waveforms and one or more stimulation fields, or at least certain aspects of the pattern). The stimulation configuration may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 820, which represents an example of stimulation control circuit 320.

Stimulation control circuit 820 can determine the stimulation configuration and determine one or more stimulation field models (SFMs) each representing a volume of tissue activated by delivering neurostimulation according to the stimulation configuration. In various embodiments, such a volume may be estimated for a set of stimulation parameters based on modeling of electrodes and tissue. Examples of such modeling and volume estimation are discussed in U.S. Pat. No. 8,190,250 B2, entitled "SYSTEM AND METHOD FOR ESTIMATING VOLUME OF ACTIVATION IN TISSUE", U.S. Pat. No. 8,706,250 B2, entitled "NEUROSTIMULATION SYSTEM FOR IMPLEMENTING MODEL-BASED ESTIMATE OF NEUROSTIMULATION EFFECTS", U.S. Pat. No. 8,934,979 B2, entitled "NEUROSTIMULATION SYSTEM FOR SELECTIVELY ESTIMATING VOLUME OF ACTIVATION AND PROVIDING THERAPY", U.S. Pat. No. 9,792,412 B2, entitled "SYSTEMS AND METHODS FOR VOA MODEL GENERATION AND USE", all assigned to Boston Scientific Neuromodulation Corporation, which are incorporated by reference herein in their entirety.

In various embodiments, stimulation control circuit 820 can generate SFM data representing the one or more SFMs, visually present the one or more SFMs using presentation device 856 based on the SFM data, and store the SFM data in external storage device 818 to be used for analysis when needed. The one or more SFMs, without additional data, do not indicate a stimulation effect type (e.g., anodic or cathodic stimulation field) underlying each SFM. In other words, the activated volume itself does not indicate what stimulation effect type activates it.

The stimulation effect type includes a type of stimulation effected from delivery of neurostimulation according to the stimulation configuration. In one embodiment, the stimulation effect type underlying each SFM includes one or more features measurable from one or more voltage profiles representing the stimulation field at one or more points within the SFM. For example, the voltage profile for a point within the SFM being a voltage signal measured at the point and showing a pulse resulting from delivery of a neurostimulation pulse. In an example of an existing system, the SFM is not tagged with the underlying stimulation effect type (e.g., the one or more features measurable from one or more voltage profiles), and the visually presented SFM does not indicate the underlying stimulation effect type. Though the SFM can be associated with the stimulation configuration, the stimulation effect type is lost (not stored) and not visually indicated, if it is not recorded in association with the SFM. The present subject matter provides for SFM data representing SFMs each tagged with one or more underlying stimulation effect type, thereby allowing for presentation and analysis of the SFMs with indications of their underlying stimulation effect type(s).

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figure 9:
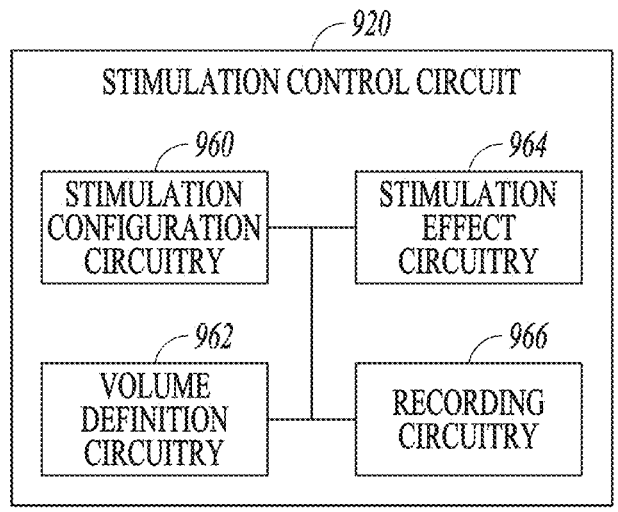
FIG. 9 illustrates an embodiment of a system for analyzing effects of neurostimulation that can be implemented in an external programming device, such as the external programming device of claim 8.

FIG. 9 illustrates an embodiment of a system for analyzing effects of neurostimulation that can include stimulation configuration circuitry 960, volume definition circuitry 962, stimulation effect circuitry 964, and recording circuitry 966. In various embodiments, this system can be implemented in an external programming device such as external programming device 802. In the illustrated embodiment, this system is part of a stimulation control circuit 920, which represents an example of stimulation control circuit 320 or 820.

Stimulation configuration circuitry 960 can determine the stimulation configuration. Volume definition circuitry 962 can determine one or more SFMs each representing a volume of the patient's tissue activated by the delivery of the neurostimulation according to the stimulation configuration. Stimulation effect circuitry 964 can determine a stimulation effect type for each tagging point specified for the one or more SFMs and can tag the one or more SFMs at each tagging point with the stimulation effect type determined for that tagging point. The stimulation effect type for each tagging point is a type of stimulation resulting from the delivery of the neurostimulation according to the stimulation configuration as measured at that tagging point. Recording circuitry 966 can generate SFM data representing the determined one or more SFMs with the stimulation effect type tagged at each tagging point. The SFM data allow for analysis and/or presentation of the one or more SFMs with information on the stimulation effect type underlying each of the one or more SFMs.

In one embodiment, stimulation effect circuitry 964 determines a voltage profile for a tagging point. The voltage profile is a voltage signal measured at the tagging point and representative of the stimulation field at the tagging point. Stimulation effect circuitry 964 extracts one or more features as representation of the stimulation effect type from the voltage profile and/or one or more derivatives of the voltage profile.

Figure 10:
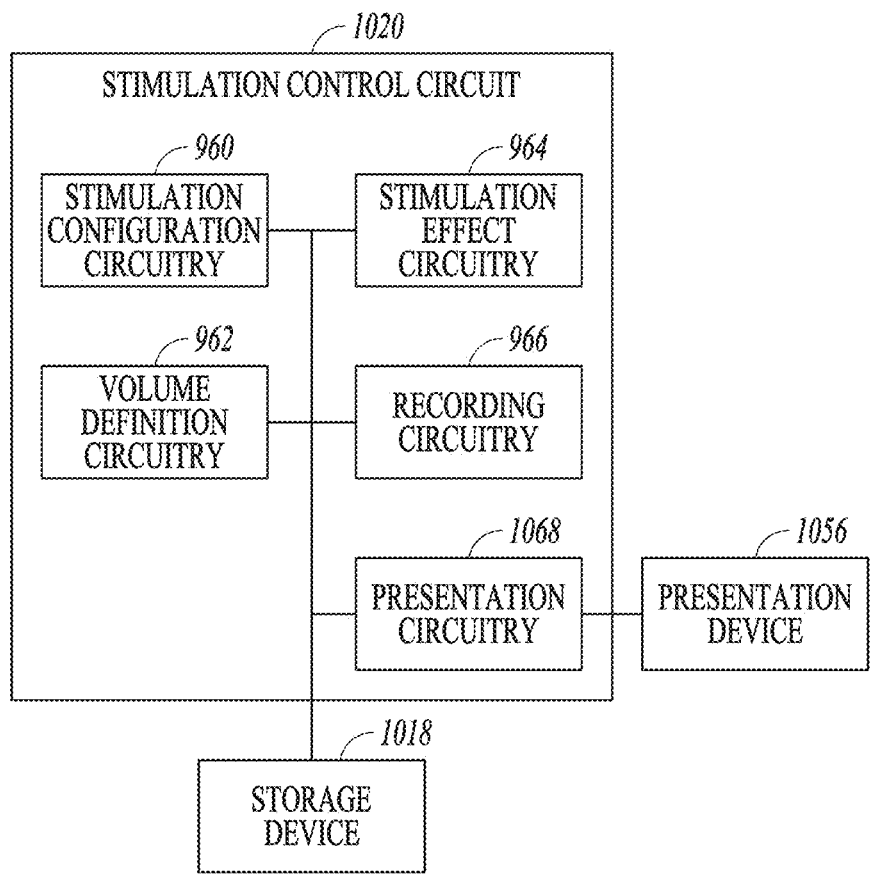
FIG. 10 illustrates another embodiment of a system for analyzing effects of neurostimulation that can be implemented in an external programming device, such as the external programming device of claim 8.

FIG. 10 illustrates another embodiment of a system for analyzing effects of neurostimulation that can be implemented in an external programming device such as external programming device 802. This system can include the system illustrated in FIG. 9 (including stimulation configuration circuitry 960, volume definition circuitry 962, stimulation effect circuitry 964, and recording circuitry 966) and presentation circuitry 1068, presentation device 1056, and storage device 1018. In the illustrated embodiment, stimulation configuration circuitry 960, volume definition circuitry 962, stimulation effect circuitry 964, recording circuitry 966, and presentation circuitry 1068 are part of a stimulation control circuit 1020, which represents another example of stimulation control circuit 320 or 820. When the system is implemented in external programming device 802, stimulation control circuit 1020 is implemented in stimulation control circuit 820, presentation device 856 can be used as presentation device 1056, and external storage circuit 818 can be used as storage device 1018.

Stimulation control circuit 1020 can determine the stimulation configuration and analyze one or more effects of the stimulation configuration. In addition to the structure and functions of stimulation control circuit 920, stimulation control circuit 1020 further includes presentation circuitry 1068, which can present the one or more SFMs with visual indication of the stimulation effect type associated with each tagging point on presentation device 1056 using the SFM data produced by recording circuit 966. In various embodiments, recording circuit 966 stores the SFM data in storage device 1018 for presentation and/or analysis.

In various embodiments, presentation circuitry 1068 presents on a display screen of presentation device 1056 visually distinctive features each assigned to a stimulation effect type. Examples of the visually distinctive features can include various degrees of shading (grayscale), various degrees of opacity, various textures (filling patterns), and various colors. In one embodiment in which the stimulation effect type includes polarity, presentation circuitry 1068 presents on the display screen the one or more SFMs with a continuum of grayscale, color, or other visual indicator representing the continuum of polarity for each tagging point using the SFM data, at a resolution determined by the resolution of grid points or voxels.

Figure 11:
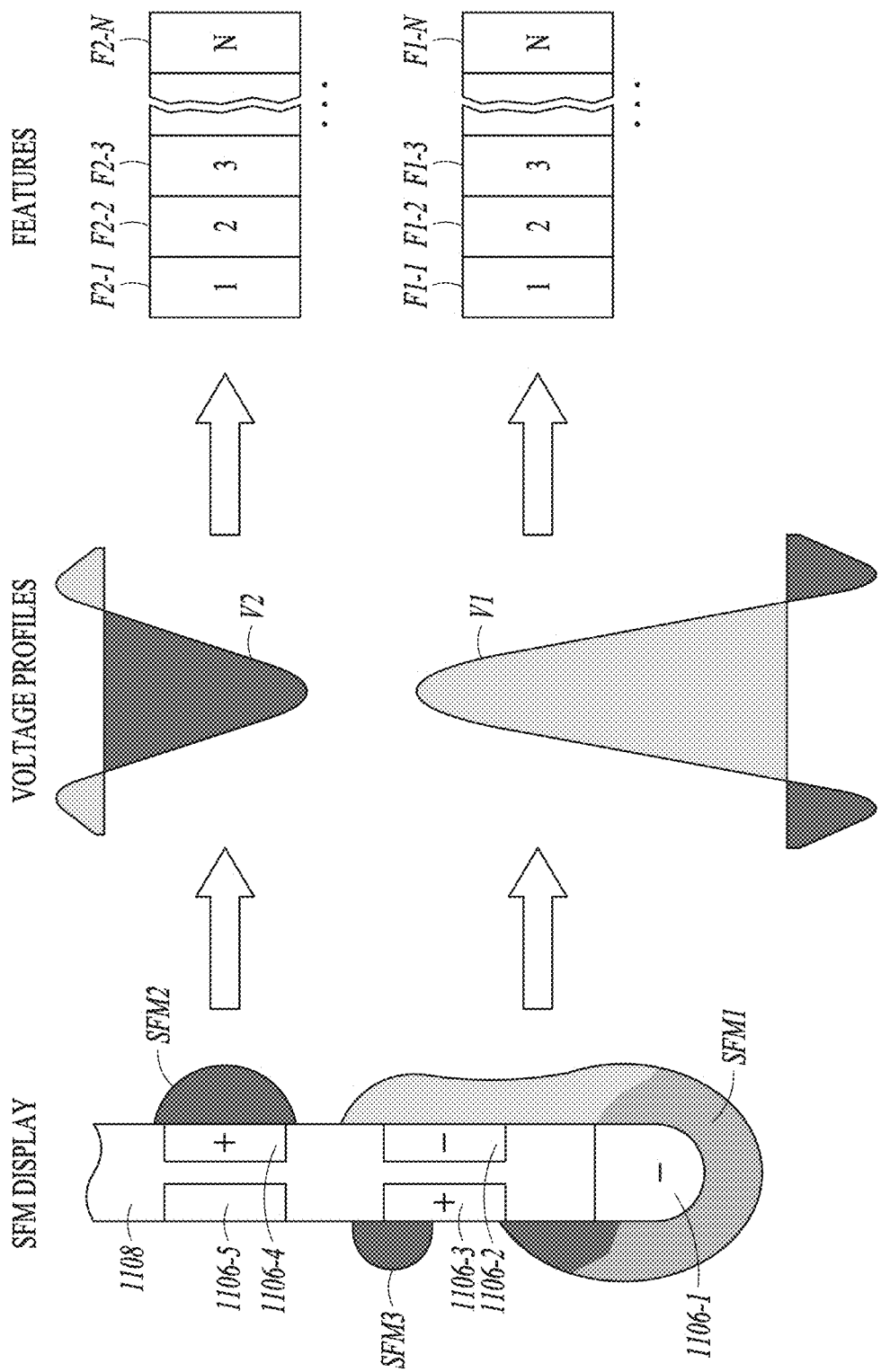
FIG. 11 illustrates an embodiment of a method for representing and recording stimulation field models tagged with stimulation effect types.
Figure 12:
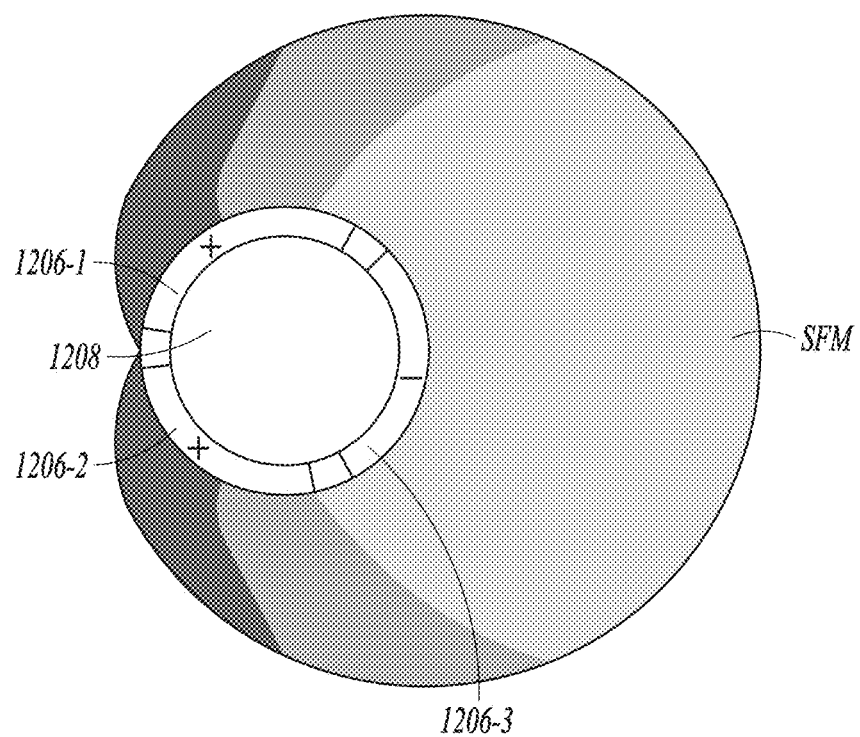
FIG. 12 illustrates an embodiment of the method of FIG. 11 showing another view of a stimulation field model.

FIG. 11 illustrates an embodiment of a method for representing and recording stimulation field models tagged with stimulation effect types. FIG. 11 illustrates an SFM display that can be shown on the display screen of presentation device 1056. The SFM display shows a portion of a lead 1108 with visible electrodes 1106-1, 1106-2, 1106-3, 1106-4, and 1106-5 and three SFMs (SFM1, SFM2, and SFM3) resulting from delivering neurostimulation through active electrodes 1106-1, 1106-2, 1106-3, and 1106-4. Electrodes 1106-1 and 1106-2 are used as cathodes (labeled "−"), and electrodes 1106-3 and electrodes 1106-4 are used as anodes. The SFMs are displayed with various degrees of shading (grayscale) presenting their polarities as the stimulation effect type. FIG. 12 illustrates an embodiment of the method of FIG. 11 showing a transverse view of the SFM display showing a portion of a lead 1208 with visible electrodes 1206-1, 1206-2, and 1106-3 and a resulting from delivering neurostimulation using electrodes 1106-1 and 1106-2 as anodes and 1106-3 as a cathode.

The various degrees of shading (grayscale) as illustrated in FIGS. 11 and 12, or any other visually distinctive features, represent the stimulation effect types underlying the SFMs. In various embodiments, the stimulation effect types can include a continuum of polarity (e.g., represented by a value of polarity between −1 (cathodic) to +1 (anodic)) and are presented in with the corresponding responses (volumes of tissue activated).

In one embodiment, stimulation effect circuitry 964 also tags phases of a neurostimulation pulse to each tagging point. Such phases of the neurostimulation pulse can further distinguish the stimulation effect types. A simple neurostimulation pulse has a single active phase that can be anodic (a) and cathodic (c). Substantially different SFMs can result from a neurostimulation pulse programmable for multiple active phases and can be desirable. In one example, a neurostimulation pulse can have 5 programmable phases (pre-phase, phase 1, interphase, phase 2, phase 3). A simple cathodic pulse can be programmed as (-,c,-,-,-), i.e.: no pre-pulse, cathodic phase 1, interphase neither anode nor cathode, no phase 2, passive phase 3. An anodic pre-pulse can be added by programming the pulse as (a,C,-,-,-), i.e.: an anodic pre-pulse, Cathodic phase 1 (capitalized letter indicating the main stimulation pulse), interphase neither anode nor cathode, no phase 2, passive phase 3.

In various embodiments, the tagging points can be SFMs (volumes, each volume is tagged once), grid points in or on the SFMs (potentially allowing each volume to be tagged more than once for a desirable resolution), or voxels within the SFMs (potentially allowing each volume to be tagged more than once for a desirable resolution). When the SFM is a 3-dimensional, the grid points can include points on the surface of the SFM, such as all or selected connecting points of a triangle mesh representing the surface of the SFM, or can include grid points within the SFM underlying its surface. A desired resolution in distribution of the stimulation effect types can be achieved by specifying grid points or voxels. The SFM data produced by recording circuitry 966 include data representing the stimulation effect type for each tagging point. It is noted that polarities of the electrodes cannot be used represent the stimulation effect type because they do not show the multiple polarities of the fields underlying the SFMs, the SFMs are disjoint from the lead, it is difficult to weight polarities of the electrodes to polarities of the SFM, and the polarities of the electrodes do not allow for grading the responses across space.

Referring to FIG. 11, after the tagging points are defined, stimulation effect circuitry 964 can determine the stimulation effect type for each tagging point and tag the SFMs at each tagging point with the stimulation effect type determined for that tagging point. In the illustrated embodiment, stimulation effect circuitry 964 determines a voltage profile for each tagging point, with two examples V1 and V2 shown under "voltage profiles" in FIG. 11. V1 represents an example of a voltage profile determined for a tagging point within SFM1. V2 represents an example of a voltage profile determined for a tagging point within SFM2. Stimulation effect circuitry 964 can then extract one or more features from each voltage profile and/or one or more derivatives of each voltage profile. Parameter(s) representing the extracted feature(s) is(are) representative of the stimulation effect type at the tagging point. As illustrated in FIG. 11, under "features", N (N≥1) features are extracted from each voltage profile. Thus, features F1-1, F1-2, F1-3, . . . F1-N are extracted from V1, and features F2-1, F2-2, F2-3, F2-N are extracted from V2. This is repeated for all the tagging points specified. In various embodiments, the number and type of the features to be extracted can be determine based on the desirability of information and cost (computational power).

Examples of the features that can be extracted from the voltage profile are shown in Table 1.

TABLE 1

Examples of Features Measured from a Voltage Profile.

| Parameter | Description |
| --- | --- |
| MAX | Maximum value of the voltage profile. |
| MIN | Minimum value of the voltage profile. |
| STD | Standard deviation of the voltage profile. |
| CENTRAL | Value at the central node of the voltage profile. |
| MAXABS | Maximum of the absolute values of the voltage profile. |
| RANGE | Difference between maximum and minimum values of the voltage profile. |
| AREAN | The area under the negative portions of the voltage profile with all points > 0 set to 0; expressed as a negative number. |
| AREAP | The area under the positive portions of the voltage profile with all points < 0 set to 0; expressed as a positive number. |
| AREAT | Total area under the profile expressed as an absolute value. |
| AREAD | Net effective area under the profile. |
| EXT | Most extreme value (farthest from zero) of the profile. Note that although its magnitude is the same as that of MAXABS, it may have a sign difference (when MIN is greater than MAX). |

In various embodiments, each parameter in Table 1 can be measured from the voltage profile (V) and/or one or more derivatives of the voltage profile (first derivative $\Delta V$, second derivative $\Delta^2 V$, third derivative $\Delta^3 V$, fourth derivative $\Delta^4 V$, . . . ). Stimulation effect circuitry 964 can measure any one or any combination of these parameters for each tagging point to represent the stimulation effect type. For example, stimulation effect circuitry 964 can measure for each tagging point a set of 10 parameters including MAX from $\Delta^2 V$, CENTRAL from $\Delta^2 V$, $\Delta^3 V$, and $\Delta^4 V$, MAXABS from V, AREAP from $\Delta^2 V$, AREAD from $\Delta^2 V$, and EXT from $\Delta^2 V$, $\Delta^3 V$, and $\Delta^4 V$.

In various embodiments, recording circuitry 966 can group the SFM data based on the stimulation effect type tagged on the SFMs. This solves the problem of grouping the SFMs overlapping in common space for analysis, when their stimulation effect types differ. For example, it can be desirable to treat anodic and cathodic volumes differently when performing a sweet-spot analysis (for determining an optimal stimulation target site). Because the stimulation configuration alone does not indicate the resulting stimulation effect types, the present subject matter provides more information for improved analysis and selection of the stimulation configuration by tagging each SFM, or preferably each grid point or voxel within each SFM, with the stimulation effect type.

Figure 13:
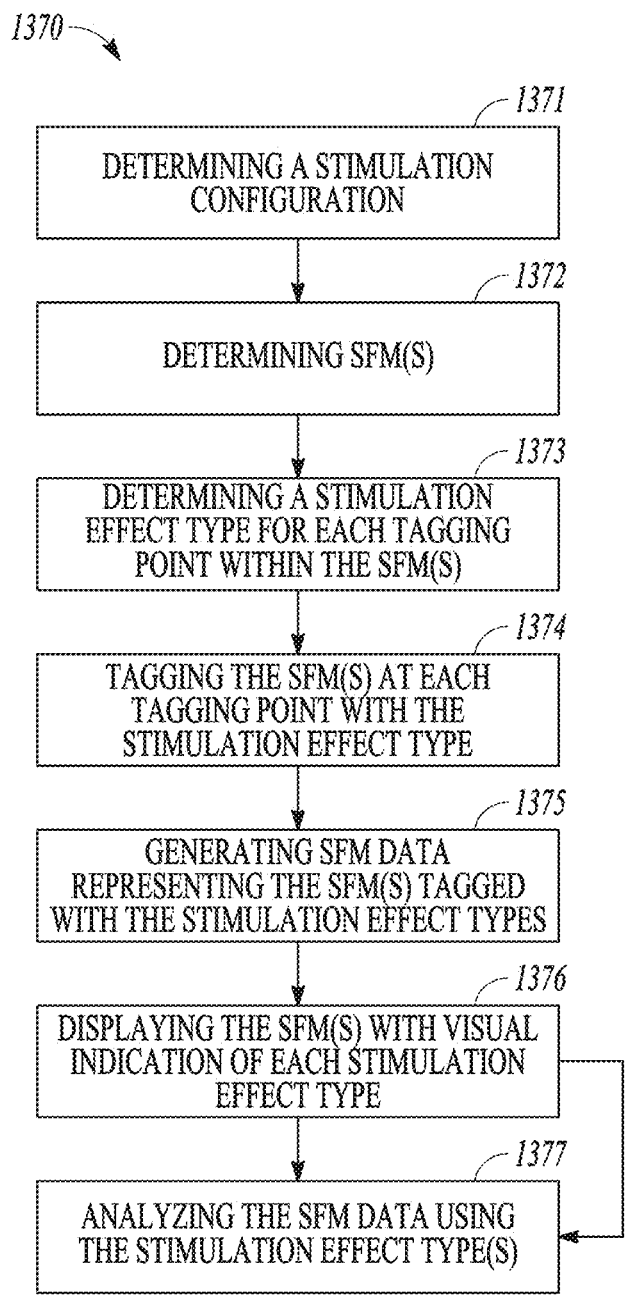
FIG. 13 illustrates an embodiment of a method for analyzing effects of neurostimulation.

FIG. 13 illustrates an embodiment of a method 1370 for analyzing effects of neurostimulation. In one embodiment, method 1370 is performed using stimulation control circuit 1020. For example, stimulation control circuit 1020 can include a processor programmed to perform selected or all the steps of method 1370. Storage device 1010 can include a non-transitory computer-readable storage medium including instructions, which when executed by the processor, cause the processor to perform method 1370. In various embodiments, method 1370 is performed for programming a stimulation device to deliver neurostimulation to tissue of a patient according to a stimulation configuration.

At 1371, a stimulation configuration is determined. To programming the stimulation device, a plurality of stimulation parameters is generated for controlling delivery of the neurostimulation according to the stimulation configuration. The stimulation can then deliver the neurostimulation one or more electrodes of a plurality of electrodes in a lead system according to the stimulation configuration, which specifies stimulation waveforms and fields (electrode arrangements).

At 1372, one or more SFMs are determined. The one or more SFMs each represent a volume of the patient's tissue activated by the delivery of the neurostimulation according to the stimulation configuration.

At 1373, a stimulation effect type for each tagging point specified for the one or more SFMs is determined. The stimulation effect type for each tagging point can be a type of stimulation resulting from the delivery of the neurostimulation according to the stimulation configuration as measured at that tagging point. In one embodiment, the stimulation effect type includes a polarity. In another embodiment, the stimulation effect type includes a neurostimulation pulse type. In one embodiment, determining the stimulation effect type includes determining a voltage profile for each tagging point. The voltage profile is a voltage signal measured at the tagging point and representative of the stimulation field at the tagging point. Determining the stimulation effect type further includes extracting one or more features as a representation of the stimulation effect type from at least one of the voltage profile or one or more derivatives of the voltage profile. Examples of such one or more features can include the polarity of the voltage profile and/or the features in Table 1. In various embodiments, determining the stimulation effect type for each tagging point can include determining the stimulation effect type for each SFM. When a better resolution is desired, determining the stimulation effect type for each tagging point can include determining the stimulation effect type for each grid point or voxel within each SFM.

At 1374, the one or more SFMs are tagged at each tagging point with the stimulation effect type determined for that tagging point. At 1375, SFM data are generated. The SFM data represent the one or more SFMs with the stimulation effect type tagged at each tagging point in the one or more SFMs. Performance of method 1370 can stop at this point with the SFM data saved for later use.

Method 1370 can optionally include steps 1376 and/or 1377, which are illustrated in FIG. 13. At 1376, the one or more SFMs are presented with visual indication of the stimulation effect type for each tagging point in the one or more SFMs on a display screen. The stimulation effect type is visually indicated by displaying visually distinctive features assigned to various stimulation effect types on the display screen. For example, the visually distinctive features can include various degrees of shading (grayscale), various degrees of opacity, various textures, or various colors. At 1377, the SFM data is analyzed using the stimulation effect type(s). For example, SFMs or portions of the SFMs may be grouped by the stimulation effect types for analysis. In one embodiment, a single device includes a processor programmed to perform method 1370 including all the illustrated steps. In other embodiments, two or more devices include processors programmed to perform method 1370, with one device including a processor programmed to perform steps 1371, 1372, 1373, 1374, and 1375, and one or more other devices each including a processor programmed to perform steps 1376 and/or 1377.

In various embodiments, method 1370 can be performed to collect SFM data for evaluating stimulation configurations based on analysis of SFMs tagged with stimulation effect types. For example, using multiple polarities can enhance selectivity in DBS and when using directional leads. When the trajectory or orientation of a test neural element in space affects its response to neurostimulation, tagging voxels with stimulation effect types can allow for a more refined analysis.

Some examples of performing steps 1376 and/or 1377 using the SFM data generated at 1375 in stimulation device programming are discussed below. In various embodiments, the SFM data generated using the present system and method meet the requirement of these examples, but are not limited by meeting such requirements.

In one example, while programming a stimulation device, the SFM(s) associated with the stimulation parameters are displayed with visual indicators (e.g., with colors or grayscale for polarity) of the stimulation effect type(s) underlying the SFM(s). The SFM(s) and the visual indicators are modified as the stimulation parameters are modified.

In another example, SFM data was saved from a previously programmed or planned stimulation. Using the same device that generated the SFM data or a different device to which the SFM data was exported to, the SFM(s) represented in the SFM data are displayed with visual indicators (e.g., with colors or grayscale for polarity) of the stimulation effect type(s) underlying the SFM(s).

In yet another example, SFMs from multiple previously programmed or planned stimulation can be combined by controlling the joining of the SFMs based on their underlying stimulation effect types (e.g., grouping by selecting only 100% cathodic regions, regions with over 60% cathodic effect, or regions of only mixed polarity effect). For example, 10 SFMs, including 6 SFMs with only the cathodic regions and 4 SFMs with only the mixed regions, can be combined to compare these subsets. Similarly, SFMS with regions of cathode effect and SFMs with regions of anode effect and depolarizing pre-pulse effect can be combined to compare these sub sets.

In these two examples, some data are presented directly (e.g., automatically, such was the visual indicators using colors or grayscale for polarity), while other data can be presented in a different format and/or in response to a user command (e.g., presenting a pop-up textbox showing data measured from the voltage profile in response to the user clicking on a point on a surface of a displayed SFM).

In these examples, the visual indicators can be produced at the time of generating the SFM data and saved with the SFM data by the device that generates the SFM data, or at the time of presentation by another device to which the SFM data was exported to. Once the SFM data are generated at 1375 by one device, they can be processed by the same device or one or more other devices each capable of performing steps 1376 and/or 1377.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to tissue of a patient, the system comprising:
   a stimulation device configured to deliver the neurostimulation; and
   a programming device configured to be communicatively coupled to the stimulation device and including:
     stimulation configuration circuitry configured to determine a stimulation configuration;
     volume definition circuitry configured to determine one or more stimulation field models (SFMs) each representing a volume of the tissue activated by the delivery of the neurostimulation according to the stimulation configuration;
     stimulation effect circuitry configured to determine a stimulation effect type for each tagging point specified for the one or more SFMs and to tag the one or more SFMs at the each tagging point with the stimulation effect type determined for that tagging point, the stimulation effect type for each tagging point being a type of stimulation resulting from the delivery of the neurostimulation according to the stimulation configuration as measured at that tagging point; and
     recording circuitry configured to generate SFM data representing the determined one or more SFMs with the stimulation effect type tagged at the each tagging point,
   wherein the programming device is configured to adjust the stimulation configuration using the SFM data and program the stimulation device to deliver the neurostimulation according to the stimulation configuration.

2. The system of claim 1, further comprising:
   a presentation device; and
   presentation circuitry configured to present the determined one or more SFMs with visual indication of the stimulation effect type for the each tagging point on the presentation device using the generated SFM data.

3. The system of claim 2, wherein the presentation device comprises a display screen, and the presentation circuitry is configured to display on the display screen visually distinctive features assigned to various stimulation effect types.

4. The system of claim 3, wherein the visually distinctive features comprise at least one of various degrees of shading, various degrees of opacity, various textures, or various colors.

5. The system of claim 1, wherein the stimulation effect circuitry is configured to determine a polarity of the stimulation effect type.

6. The system of claim 5, wherein the stimulation effect circuitry is further configured to determine a neurostimulation pulse type of the stimulation effect type.

7. The system of claim 1, wherein the stimulation effect circuitry is configured to determine a voltage profile for the each tagging point being a voltage signal measured at the tagging point and representing the stimulation field at the tagging point and to extract one or more features as a representation of the stimulation effect type from at least one of the voltage profile or one or more derivatives of the voltage profile.

8. The system of claim 1, wherein the stimulation effect circuitry is configured to determine the stimulation effect type for each SFM of the one or more SFMs.

9. The system of claim 1, wherein the stimulation effect circuitry is configured to determine the stimulation effect type for each grid point in or on the one or more SFMs or voxel within the one or more SFMs.

10. The system of claim 1, wherein the programming device comprises:
    a programming control circuit configured to generate a plurality of stimulation parameters controlling delivery of the neurostimulation according to a stimulation configuration, the neurostimulation delivered through one or more electrodes of the plurality of electrodes; and a user interface including a presentation device, a user input device, and a stimulation control circuit coupled to the presentation device and the user input device, the stimulation control circuit including the stimulation configuration circuitry, the volume definition circuitry, the stimulation effect circuitry, and the recording circuitry.

11. A method for delivering neurostimulation to tissue of a patient, the method comprising:
  determining a stimulation configuration using a processor;
  determining one or more stimulation field models (SFMs) using the processor, the one or more SFMs each representing a volume of the tissue activated by the delivery of the neurostimulation according to the stimulation configuration;
  determining a stimulation effect type for each tagging point using the processor, the each tagging point specified for the one or more SFMs, the stimulation effect type for each tagging point being a type of stimulation resulting from the delivery of the neurostimulation according to the stimulation configuration as measured at that tagging point;
  tagging the one or more SFMs at the each tagging point with the stimulation effect type determined for that tagging point using the processor;
  generating SFM data using the processor, the SFM data representing the determined one or more SFMs with the stimulation effect type tagged at the each tagging point;
  adjusting the stimulation configuration using the SFM data; and
  delivering the neurostimulation from a stimulation device according to the stimulation configuration.

12. The method of claim 11, further comprising:
  displaying the determined one or more SFMs with visual indication of the stimulation effect type for the each tagging point on a display screen; and
  displaying visually distinctive features assigned to various stimulation effect types on the display screen.

13. The method of claim 12, wherein displaying the visually distinctive features comprises displaying at least one of various degrees of shading, various degrees of opacity, various textures, or various colors.

14. The method of claim 11, wherein determining the stimulation effect type comprises determining a polarity.

15. The method of claim 11, wherein determining the stimulation effect type comprises determining a neurostimulation pulse type.

16. The method of claim 11, wherein determining the stimulation effect type comprises determining a voltage profile for the each tagging point being a voltage signal measured at the tagging point and representing the stimulation field at the tagging point.

17. The method of claim 16, wherein determining the stimulation effect type further comprises extracting one or more features as a representation of the stimulation effect type from at least one of the voltage profile or one or more derivatives of the voltage profile.

18. The method of claim 11, wherein determining the stimulation effect type further comprises determining the stimulation effect type for each SFM of the one or more SFMs.

19. The method of claim 11, wherein determining the stimulation effect type further comprises determining the stimulation effect type for each grid point in or on the one or more SFMs or voxel within the one or more SFMs.

20. A non-transitory computer-readable storage medium including instructions, which when executed by a system, cause the system to perform a method for delivering neurostimulation to tissue of a patient according to a stimulation configuration, the method comprising:
  determining a stimulation configuration;
  determining one or more stimulation field models (SFMs) each representing a volume of the tissue activated by the delivery of the neurostimulation according to the stimulation configuration;
  determining a stimulation effect type for each tagging point specified for the one or more SFMs, the stimulation effect type for each tagging point being a type of stimulation resulting from the delivery of the neurostimulation according to the stimulation configuration as measured at that tagging point;
  tagging the one or more SFMs at the each tagging point with the stimulation effect type determined for that tagging point;
  generating SFM data using the processor, the SFM data representing the determined one or more SFMs with the stimulation effect type tagged at the each tagging point;
  adjusting the stimulation configuration using the SFM data; and
  delivering the neurostimulation from a stimulation device according to the stimulation configuration.

* * * * *